United States Patent [19]

Hahn et al.

[11] Patent Number: 4,872,192
[45] Date of Patent: Oct. 3, 1989

[54] X-RAY EXAMINATION INSTALLATION FOR OPTIONAL TRANSILLUMINATION OR EXPOSURE OF AN EXAMINATION SUBJECT

[75] Inventors: Alfred Hahn, Erlangen; Jens-Peter Raup, Uttenreuth, both of Fed. Rep. of Germany

[73] Assignee: Siemens Aktiengesellschaft, Berlin and Munich, Fed. Rep. of Germany

[21] Appl. No.: 274,870

[22] Filed: Nov. 22, 1988

[30] Foreign Application Priority Data

Dec. 18, 1987 [DE] Fed. Rep. of Germany ... 8716725[U]

[51] Int. Cl.⁴ .............................................. H05G 1/02
[52] U.S. Cl. ..................................... 378/181; 378/197
[58] Field of Search ............... 378/181, 196, 197, 195, 378/167

[56] References Cited

U.S. PATENT DOCUMENTS

| 4,024,401 | 5/1977 | Bernstein et al. | |
|---|---|---|---|
| 4,468,803 | 8/1984 | Ronci | 378/181 |
| 4,501,011 | 2/1985 | Hauck et al. | 378/197 |

FOREIGN PATENT DOCUMENTS

| 0205878 | 11/1971 | European Pat. Off. | |
|---|---|---|---|
| 2922960 | 3/1977 | Fed. Rep. of Germany | |
| 56-155937 | 4/1977 | Japan | |

OTHER PUBLICATIONS

Siemens Brochure for ANGIOSKOP A33.

*Primary Examiner*—Craig E. Church
*Attorney, Agent, or Firm*—Hill, Van Santen, Steadman & Simpson

[57] ABSTRACT

An x-ray examination installation permits a transillumination image, or an x-ray exposure of an examination subject to be optionally undertaken. The installation includes a C-bend adjustable in position relative to an examination subject, with an x-radiator and a x-ray image intensifier being respectively melted at opposite free ends of the C-bend. The x-ray image intensifier is used for transillumination of the subject, and an exposure device such a sheet film changer, is positionable opposite the x-ray source for producing an exposure. The exposure device is held spatially freely adjustable relative to the C-bend by a carrying device. The exposure device is connectable to the C-bend with a releasable coupling mechanism so that the exposure device follows movements of the C-bend without changing its position relative to the x-radiator.

10 Claims, 2 Drawing Sheets

X-RAY EXAMINATION INSTALLATION FOR OPTIONAL TRANSILLUMINATION OR EXPOSURE OF AN EXAMINATION SUBJECT

BACKGROUND OF THE INVENTION

1. Field of the Invention

The present invention is directed to x-ray examination installation which permits an x-ray examination subject optionally to be examined in a transillumination mode, or to have an x-ray exposure of a selected region produced.

X-ray examination installations which offer the possibility of producing a direct exposure of a diagnostically relevant region of a patient, the region being perceptible is a transillumination mode of the patient, are known in the art. An example of such an x-ray examination installation is described in the advertising brochure for "ANGIOSKOP A33" manufactured by Siemens Elema AB, Sweden. This installation has a x-ray diagnostics device including an adjustable C-bend with an x-radiator mounted at one end, and an x-ray image intensifier, for transillumination of the examination subject mounted at the opposite end. An exposure device is positionable opposite the x-radiator to obtain a radiographic exposure of the examination subject.

A sheet film changer is used as the exposure device, and is attached to the x-ray diagnostics device so as to be joined with the x-ray image intensifier to form a unit therewith which is pivotable around an axis so that either the x-ray image intensifier or the exposure is positionable opposite the x-radiator. This known thus permits a change from a transillumination mode to an exposure mode to be undertaken in a simple manner, by merely pivoting the unit consisting of the x-ray image intensifier and the exposure device to bring one of those components into the radiation field. The exposure device also follows arbitrary movements of the x-ray diagnostics device, because it is connected to the x-ray image intensifier, which is turn connected to the x-ray diagnostics device. A disadvantage is present in this installation, however, because the C-bend of the x-ray diagnostics device is loaded not only by the weight of the x-ray image intensifier and the x-radiator, but also by the weight of the exposure device. The C-bend and the bearing thereof, must consequently be solidly built, resulting in additional costs. Moreover, the unit consisting of the x-ray image intensifier and exposure device restricts the accessibility of the attendant or physician to the examination subject in certain examinations as a consequence of its considerable space requirements.

SUMMARY OF THE INVENTION

It is an object of the present invention to provide an x-ray examination installation of the type described above wherein the C-bend of the x-ray diagnostics device is relieved of the weight of the exposure device, and which permits improved accessibility to the examination subject.

It is a further object of the present invention to provide such an x-ray examination installation which nonetheless assures that a simple change from the transillumination mode to the exposure mode is possible.

Another object of the present invention is to provide such an x-ray examination installation wherein the exposure device can follow arbitrary movements of the x-ray diagnostics device.

The above object is achieved in accordance with the principles of the present invention in an x-ray examination installation wherein the exposure device is held by a carrier in a spacely freely adjustable manner with respect to the x-ray diagnostics device, with the exposure device being connected to the x-ray diagnostics with a releasable coupling mechanism. The coupling mechanism permits the exposure device to follow the movements of the x-ray diagnostics device without changing its position relative to the x-radiator. Because a carrier is provided for the exposure device, the C-bend of the x-ray diagnostics device is relieved of the weight of the exposure device. Moreover, improved accessibility to the examination subject results because the exposure device need only be connected to the x-ray diagnostics device with the releasable coupling mechanism when it is required for producing an exposure. A simple change from the transillumination mode to the exposure is assured because the exposure device merely must be joined to the x-ray diagnostics device with the coupling mechanism. Moreover, the coupling mechanism is fashioned so that the x-ray exposure device, held at the carrier in a freely adjustable fashion, follows arbitrary movements of the x-ray diagnostics device.

In one embodiment of the invention, the carrier permits the exposure device to be moved to a standby position outside of the range of adjustment of the x-ray diagnostics device when the coupling mechanism is released. It is thus assured that the exposure device, when separated from the x-ray diagnostics device, does not constitute an impediment to the movements of the x-ray diagnostics device.

The C-bend is pivotable around a first axis proceeding in the plane of the C-bend, and is also pivotable around a second axis proceeding perpendicularly to the plane of the C-bend. The two axes intersect at an isocenter around which the C-bend is pivotable, and through which the central ray of the x-ray beam from the x-radiator proceeds. The exposure device is attached to the carrier pivotable around a third axis proceeding parallel to the first axis and also pivotable around a fourth axis proceeding parallel to the second axis. The exposure device can thus follow the movements of the x-ray diagnostics device, i.e. of the C-bend in the required manner.

The coupling mechanism may consist of a coupling rod by which the exposure device can be rigidly connected to the x-ray diagnostics device, so that it is assured that the coupling device retains its position relative to the x-radiator of the x-ray diagnostics device.

The carrier may have an arm to which the exposure device is attached, with the arm being pivotable together with the carrier around the third axis, and being rigidly connected to the exposure device relative to that axis. The exposure device is connected to the arm so as to be pivotable around the fourth axis, the arm being rigidly connected to carrier with the respect to the axis. It is thus assured in a structurally simple manner that the exposure device can execute the required swivel movements with respect to the third and the fourth axes.

The carrying device may include a weight compensation system to compensate for the weight of the expose device, so that it is possible to move the exposure device toward the x-ray diagnostics device with little exertion of force, and to connect it thereto. The carrier may also be provided with a device for compensating the torque generated by the weight of the exposure device relative to the third and/or fourth axis. An especially simple embodiment of the x-ray examination installation of the invention results if the fourth axis proceeds through the center of gravity of the exposure device, because the weight of the exposure device can then produce no torque with respect to this axis.

To assure the required, free spatial adjustability of the exposure device, the carrier may be in the form of a ceiling melt with a downwardly telescoping column, the upper end of the telescoping column being attached to a carriage which is displaceable along a rails. Those rails are in turn displaceable along ceiling-mounted rails which proceed transversely relative thereto. The exposure device is attached to the lower free end of the telescoping column. It is preferable that an arm of the carrier in this embodiment be attached to the free end of the telescoping column so as to be pivotable around the third axis, and that this arm has length so that the C-bend is pivotable around the first axis by at least 15° in both directions without hitting the carrier, because all critical examinations can be then undertaken with this x-ray examination installation.

DESCRIPTION OF THE PREFERRED EMBODIMENTS

Figure 1:
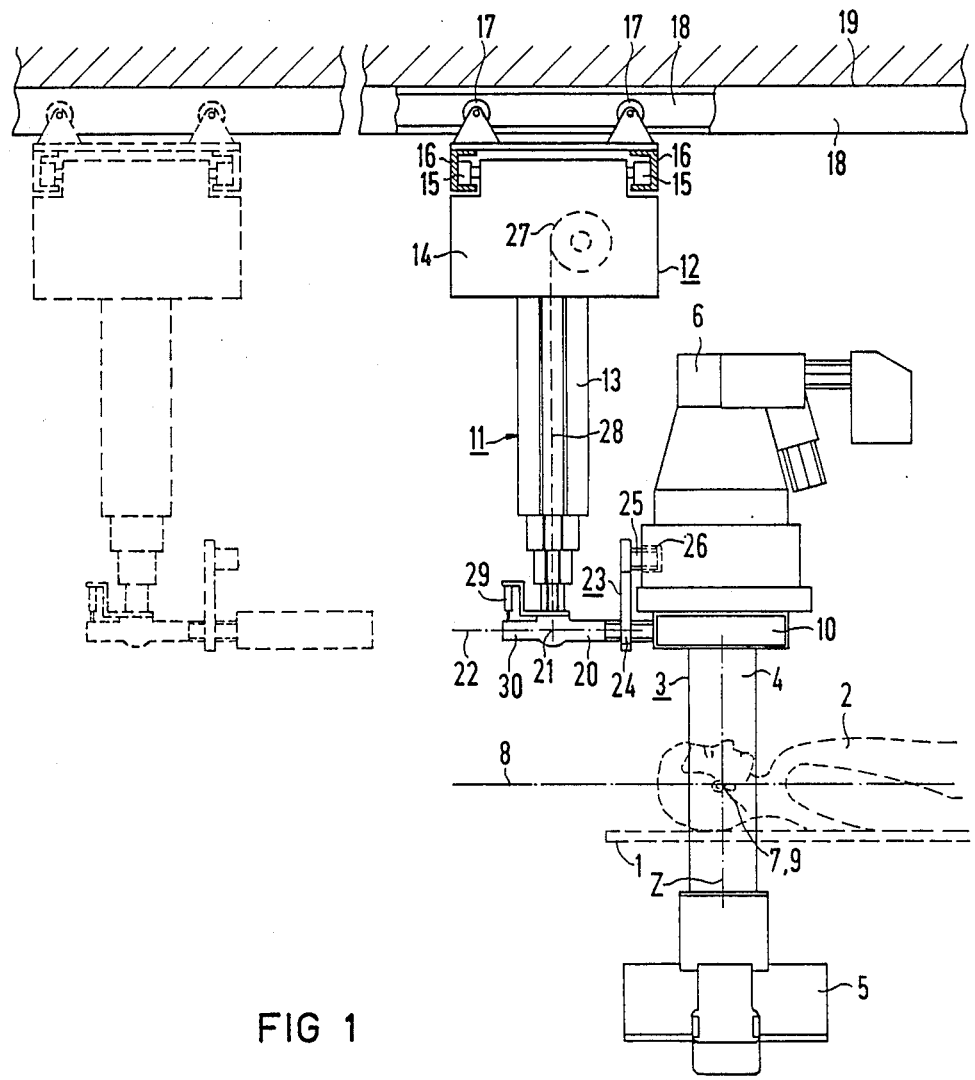
FIG. 1 is a side view of an x-ray examination installation constructed in accordance with the principles of the present invention.

An x-ray examination installation constructed in accordance with the principles of the present invention for optional transillumination or exposure of an examination subject 2, indicated in dashed lines, is shown in FIG. 1. The patient 2 lies on a patient support table 1. The installation includes an x-ray diagnostics device generally referenced 3, which is adjustable relative to the examination subject 2. The x-ray diagnostics device includes a C-bend 4 having one free end at which an x-radiator 5 is mounted, and an opposite free end and which an x-ray image intensifier 6 in mounted for transillumination of the examination subject 2 disposed between the x-radiator 5 and the x-ray image intensifier 6.

Figure 2:
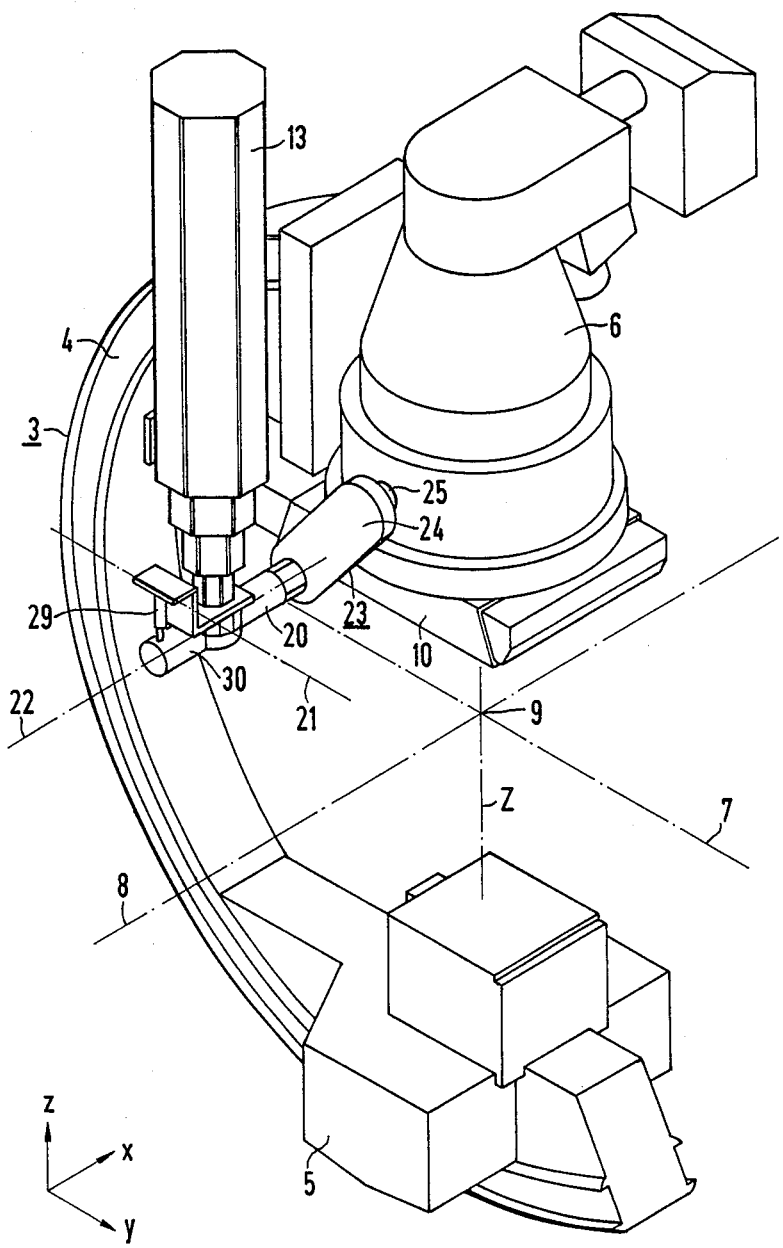
FIG. 2 is a perspective view of the x-ray examination installation shown in FIG. 1.

The C-bend 4 is attached to a mount (not shown in the drawings) of the type known to those skilled in the art so as to be pivotable around a first axis 7 proceeding out of the plane of the drawing in FIG. 1 and shown in perspective in FIG. 2. The first axis 7 is in the plane of the C-bend 4. The C-bend 2 is also pivotable around a second axis 8, proceeding perpendicular to the plane of the C-bend 4. The C-bend 4 is also adjustable in the direction of the 3 spacial axes x, y and z, which are indicated in FIG. 2. The two axes 7 and 8 intersect at an isocenter 9 around which the C-bend 4 in pivotable, and through which a central ray Z (indicated in dot-dash lines) of an x-ray beam emanating from the x-radiator 5 proceeds. For undertaking an examination, the x-ray diagnostics device 3 is positioned relative to the examination subject 2 so that a diagnostically relevant region of the subject 2 is situated at the isocenter 9. By swivelling the C-bend 4 around the axes 7 and 8, the diagnostically relevant region can then be transirradiated from different directions.

An exposure device 10, such as a sheet film changer, is positionable opposite the x-radiator 5, which permits preparation of an x-ray exposure as needed, of the diagnostically relevant region of the x-ray examination subject 2. The region of the exposure can be selected during the transillumination mode, wherein the image can be made visible a video display system (not shown).

The exposure device 10 is attached to a carrier, generally referenced 11, which includes a ceiling mount 12 with a telescoping column 13. As shown in FIG. 1, the upper end of the column 13 is attached to a carriage 14, which is displaceable along two parallel rails 16 which respectively receive rollers 15. The rails 16 are in turn displaceable by rollers 17 along two ceiling-mounted rails 18 proceeding parallel to each other, and which are attached to the ceiling 19 of the examination room transversely relative to the rails 16. Because the exposure device 10 is attached to the lower end of the telescoping column 13, it is adjustable in the direction of the three spatial axes x, y, z using the ceiling mount 12.

The exposure device 10 is attached to the lower end of the telescoping column 13 with an arm 20, which is a part of the carrier 11. By means of an articulation of the type known to those skilled in the art, which is not shown in detail in the drawings, the arm 20 is connected to the lower end of the telescoping column 13 so as to be pivotable around a third axis 21 which proceeds parallel to the first axis 7. The arm 20 is rigidly connected to the exposure device 10 with respect to the axis 21. The arm 20 is pivotally connected, by means of another articulation of the type known to those skilled in the art, to the exposure device 10 with respect to a fourth axis 22 which proceeds parallel to the second axis 8. The arm 20 is rigidly attached to the column 13 with respect to the axis 22. The exposure device 10 is thus adjustable with the carrier 11 not only in the direction of the three spatial axes x, y, z, as already described, but also is pivotable around the third axis 21 and around the fourth axis 22, and is therefor freely adjustable with respect to the x-ray diagnostics device 3.

The x-ray diagnostics installation also includes a releasable coupling mechanism 23 connecting the exposure device 10 to the x-ray diagnostics device 3. The coupling mechanism 23 includes a coupling rod 24 having one end rigidly attached to the arm 20, and having a projection 25 at its other end which is engagable into a corresponding bore 26 in the x-ray image intensifier 6 of the x-ray diagnostics device 3. The exposure device 10 can thus be rigidly connected to the x-ray diagnostics device 3 of the coupling rod 24. When the projection 25 is received in the bore 26, the exposure device 10 is arranged in a position opposite the x-radiator 5 required for producing an exposure. Because the exposure device 10 is rigidly connectable to the x-ray diagnostics 3 with the coupling mechanism 23, and because the exposure device 10 is also spacely freely adjustable with respect to the x-ray diagnostics device 3 by means of the carrier 11, the exposure device 10 coupled to the x-ray diagnostics device 3 with the coupling mechanism 23 can follow the movements of the x-ray diagnostics device 3 without changing its position relative to the x-radiator 5. This is true not only for swivel movements of the C-bend 4 of the x-ray diagnostics device 3 around the axes 7 and 8, but also for movements of the x-ray diagnostics device 3 in the direction of the three spatial axes, x, y, z.

A weight compensating system 27 is shown in dashed lines inside the carriage 4. The weight compensating system includes a cable 28 attached to the lower end of the column 13, so that the weight compensating system 27 exerts a force corresponding to the weight of the exposure device 10. A pneumatic spring 29 is also attached to the lower end of the telescoping column 13. The pneumatic spring 29 exerts a force on a portion 30 of the arm 20 extending beyond the third axis 21 (as seen proceeding from the exposure device 10) which compensates for the torque produced by the weight of the exposure device 10 with respect to the third axis 21. The fourth axis 22 proceeds through the center of gravity of the exposure device 10, so that the weight thereof cannot exert any torque with respect to the fourth axis 22.

The x-ray diagnostics device 3, and more specifically the C-bend 4 thereof, is thus completely relieved of the weight of the exposure device 10. Given adjustment of the x-ray diagnostics device 3 with the exposure device 10 coupled thereto, therefor, only those forces that are required for overcoming the mass moment of inertia and the possible frictional forces must be exerted to adjust the exposure device 10. Moreover, attending personnel can bring the exposure device 10 to the x-ray diagnostics device 3, and couple it thereto, or can separate it therefrom, with little exertion of force.

The arm 20 of the carrier 11 has a length which permits the C-bend 4 to pivotable by at least 15° around the first axis 7 in both directions.

The rails 16 and the ceiling rails 18 have a length such that the exposure device 10 can be moved to a standby position outside of the range of adjustment of the x-ray diagnostics device 3 when the coupling mechanism 23 is released, as indicated in dashed lines in FIG. 1.

Although modifications and changes may be suggested by those skilled in the art, it is the intention of the inventors to embody within the patent warranted hereon all changes and modifications as reasonably and properly come within the scope of there contribution to the art.

We claim:

1. An x-ray examination installation for optional transillumination or exposure of an examination subject, said installation comprising:
    an x-ray diagnostics device adjustable relative to said examination subject including a moveable C-bend having two free ends, and x-radiator mounted at one free end of said C-bend, and an x-ray image intensifier for transillumination of said examination subject mounted at the other free end of said C-bend;
    an exposure device movable opposite said x-radiator for producing an exposure of said examination subject;
    means for supporting said exposure device independently spacially adjustable relative to said x-ray diagnostics device; and
    means for releasably mechanically coupling said exposure device to said x-ray diagnostics device and for permitting said exposure device, when coupled to said x-ray diagnostics device, to follow movements of said x-ray diagnostics device without changing the position of said exposure device relative to said x-radiator.

2. An x-ray installation as claimed in claim 1, wherein said for means for supporting said exposure device includes means for moving said exposure device to, and supports said exposure device at a standby position remote from said x-ray diagnostics device when said means for coupling is released.

3. An x-ray examination installation as claimed in claim 1, wherein said x-radiator has a center ray emanating therefrom, and wherein said C-bend defines a plane, said installation further comprising:
    means for pivoting said C-bend around a first axis proceeding in the plane of said C-bend and for pivoting C-bend around a second axis proceeding perpendicularly to the plane of the C-bend, said first and second axes intersecting at a point through which said central ray of said x-radiator proceeds, said means for pivoting said C-bend also pivoting said C-bend around said isocenter; and
    said means for supporting said exposure device including means for pivoting said exposure device around a third axis proceeding parallel to said first axis and for pivoting said exposure device around a fourth axis proceeding parallel to said second axis.

4. An x-ray examination installation as claimed in claim 3, wherein said means for supporting said exposure device includes an arm to which said exposure device is attached, first articulation means for permitting pivoting of said arm relative to a remainder of said means for supporting around said third axis and for holding said exposure device rigidly relative to said third axis, and second articulation means for permitting pivoting of said exposure device around said fourth axis and for holding said arm rigidly relative to said remainder of said means for supporting with respect to said fourth axis.

5. An x-ray examination installation as claimed in claim 3, wherein said exposure device is supported by said means for supporting such that the weight of said exposure device generates torque relative to at least one of said third and fourth axes, and wherein said x-ray examination installation further includes means for compensating for said torque.

6. An x-ray examination installation as claimed in claim 3, wherein said means for pivoting said exposure device around a fourth axis is a means for pivoting said exposure device around a fourth axis proceeding through a center of gravity of said exposure device.

7. An x-ray examination installation as claimed in claim 3, wherein said means for supporting said exposure device includes a first arm extending along said third axis and a second arm connected to said first arm and extending along said fourth axis, said second arm having a length permitting pivoting of said C-bend by at least 15° around said first axis in both directions.

8. An x-ray examination installation as claimed in claim 1, wherein said means for coupling is a coupling rod having a projection releasable engagable with said x-ray diagnostics device.

9. An x-ray examination installation as claimed in claim 1, wherein said means for supporting said exposure device includes means for compensating for the weight of said exposure device.

10. An x-ray examination installation as claimed in claim 1, wherein said installation is disposed in a room having a ceiling, said installation further comprising a first set of rails mounted on said ceiling, and wherein said means for supporting said exposure device is a means for supporting said exposure device from said ceiling and compromises:
    a second set of rails extending transversely relative to said first set or rails; means for moving said second set of rails along
    said first set of rails;
    a carriage;
    means for moving said carriage along said second set of rails; and
    a telescoping arm extending downwardly from said carriage and connected to said exposure device.

* * * * *